United States Patent [19]

Hübner

[11] 4,201,200

[45] May 6, 1980

[54] APPLIANCE FOR THE CARE AND CLEANING OF TEETH AND GUMS

[76] Inventor: Otto Hübner, Mauerkircher Strasse 199, Herzog Park, Munich (8000 Munich 81), Fed. Rep. of Germany

[21] Appl. No.: 929,525

[22] Filed: Jul. 31, 1978

[30] Foreign Application Priority Data

Aug. 5, 1977 [DE] Fed. Rep. of Germany ....... 2735427
Dec. 15, 1977 [DE] Fed. Rep. of Germany ....... 2756042

[51] Int. Cl.$^2$ ............................................. A61H 9/00
[52] U.S. Cl. ....................................... 128/66; 433/29; 128/230; 206/218; 229/41 R
[58] Field of Search .................. 32/58, 40 R, DIG. 7; 128/66, 224, 229, 230; 206/218, 63.5, 577, 571, 281; 417/476, 477; 132/79 R, 79 B, 79 F; 150/49; 229/41 R

[56] References Cited

U.S. PATENT DOCUMENTS

| | | | |
|---|---|---|---|
| 1,454,388 | 5/1923 | Lauren | 150/49 |
| 2,297,799 | 10/1942 | Pifer | 32/DIG. 7 |
| 2,666,668 | 1/1954 | Sieloff | 150/49 |
| 3,316,882 | 5/1967 | Renwick | 229/41 R |
| 3,353,527 | 11/1967 | Anderson | 206/577 |
| 3,474,469 | 10/1969 | Steltz | 128/66 |
| 3,476,105 | 11/1969 | Abramowitz | 128/66 |
| 3,605,734 | 9/1971 | Igarashi et al. | 128/66 |
| 3,636,633 | 1/1972 | Fuller et al. | 32/DIG. 7 |
| 3,762,411 | 10/1973 | Lloyd et al. | 128/66 |
| 3,841,799 | 10/1974 | Spinosa et al. | 417/477 |

*Primary Examiner*—Louis G. Mancene
*Assistant Examiner*—John J. Wilson
*Attorney, Agent, or Firm*—Norman Lettvin

[57] ABSTRACT

A portable, or travel-type, oral hygiene appliance is provided with simplified and effective means for producing a pulsating, or intermittent, liquid jet; and optionally including a light stick for obtaining locally-concentrated illumination of areas within the mouth. The appliance is of lightweight and compact construction, in the form of an appliance casing having reduced vertical thickness and with a foldable water container carried on a portion of the upper surface of the casing. The pump for propelling a pulsating liquid jet uses a rotating member carrying spaced roller elements that move against a resilient, flexible, hose with a water column therein, to compress the hose between each roller and an abutment, thereby applying impeller force to spaced segments of the liquid column, so as to obtain an intermittent high pressure, liquid jet, discharge. Aspirated air is introduced into the water column upstream of the pump to aid in the interruption, or chopping, of the liquid column by the pump into pressurized pulses of liquid. A manually actuatable controller downstream of the pump operates to control volume discharge from the pump. A lighting stick, may be provided as an optional attachment, and is energized by the electrical supply for the appliance.

9 Claims, 6 Drawing Figures

APPLIANCE FOR THE CARE AND CLEANING OF TEETH AND GUMS

FIELD OF THE INVENTION

This invention relates to an improved oral hygiene appliance, to an improved pump therefor, and to improved accessories for such an appliance, such as a light stick for illuminating portions of the mouth. More particularly this invention relates to an oral hygiene appliance constructed as a compact, relatively inexpensive, portable unit especially useful for travelers, and to a rotary-type pump for producing a pulsating or intermittent liquid jet discharge.

BRIEF SUMMARY OF THE INVENTION

It has long been a practice of dentists to use a high pressure water jet, pulsed if desired, in oral hygiene for care and cleaning of teeth and gums. That same general concept, in home appliances, has been the subject of U.S. Pat. Nos. 3,227,158; 3,393,673; and 3,425,410. The devices in said patents use a reciprocating pump, and cooperating valve means in the pump, to obtain a pulsating jet, and have suggested use of a liquid container that, when not operative, may telescope with a portion of the appliance to conserve space occupied. However, the appliances of said U.S. patents are too bulky to be considered a convenient travel appliance. Furthermore, the size of such appliances and the nature of the pumps disclosed therein, are such as to forecast substantial cost and complexity both of the appliance and the pump.

Commercially available appliances, which are also called mouth showers, are already on the market. Such appliances are, however, bulky, heavy and big, and therefore unsuitable for utilization as travel appliances. So far, it has not been possible to design a compact and esthetically attractive, commercially available, appliance which is, at the same time, handy and light while having optimally small dimensions.

The cause for absence of such an appliance of a size for travel is that, either the operating parts are too bulky, for technical reasons, or the water container is too big, or both elements are just too large.

The German patent specification D-PS No. 1528 366 comes closest to a compact appliance; however, it does not meet the requirements for a travel appliance. In said German specification, a removable top is used either as a water container or as a covering device for the operating part. But, as the operating part itself is very big and very heavy, the device is not suitable as a travel appliance.

It is, therefore, an object of this invention to provide in an appliance for projecting a pulsed liquid jet, for the care and cleaning of teeth and gums, that such appliance be light, handy and of optimally small dimensions to be eventually used as a travel appliance.

Another object of this invention is to provide an improved pump construction, for use such as in an oral hygiene appliance, characterized by use of means including a rotary pumping propeller for projecting a pulsating, pressurized liquid jet.

A further object of this invention is to provide in an oral hygiene appliance an aspirating, or aerating, means for use with the liquid pump of the appliance, so as to aid in effecting discharge of a pulsating liquid jet.

Still another object of this invention is to provide, for optional use with an oral hygiene appliance, a light stick that is characterized by simplicity and inexpensiveness of construction.

And a further object of this invention is to provide an oral hygiene appliance having flexibility of usage either as a home appliance or as a travel appliance, and characterized by simplicity and inexpensiveness of construction and by effectiveness of operation.

Further objects and advantages will appear to one skilled in the art from the following description of the invention, its parts, and accessories.

In the invention, the objects are accomplished, in part, by the fact that the container for the liquid is made of a light flexible plastic so that its sides can be folded, and the other operating parts, by reason of the construction, can consequently be made smaller and lighter and be supplied by components which have not heretofore been considered for use in appliances of the type disclosed above.

Particularities and advantages of the discovery are detailed in the following description of one form of construction cited by way of example, which is represented in the drawings.

DESCRIPTION OF THE PREFERRED EMBODIMENT

Figure 1:
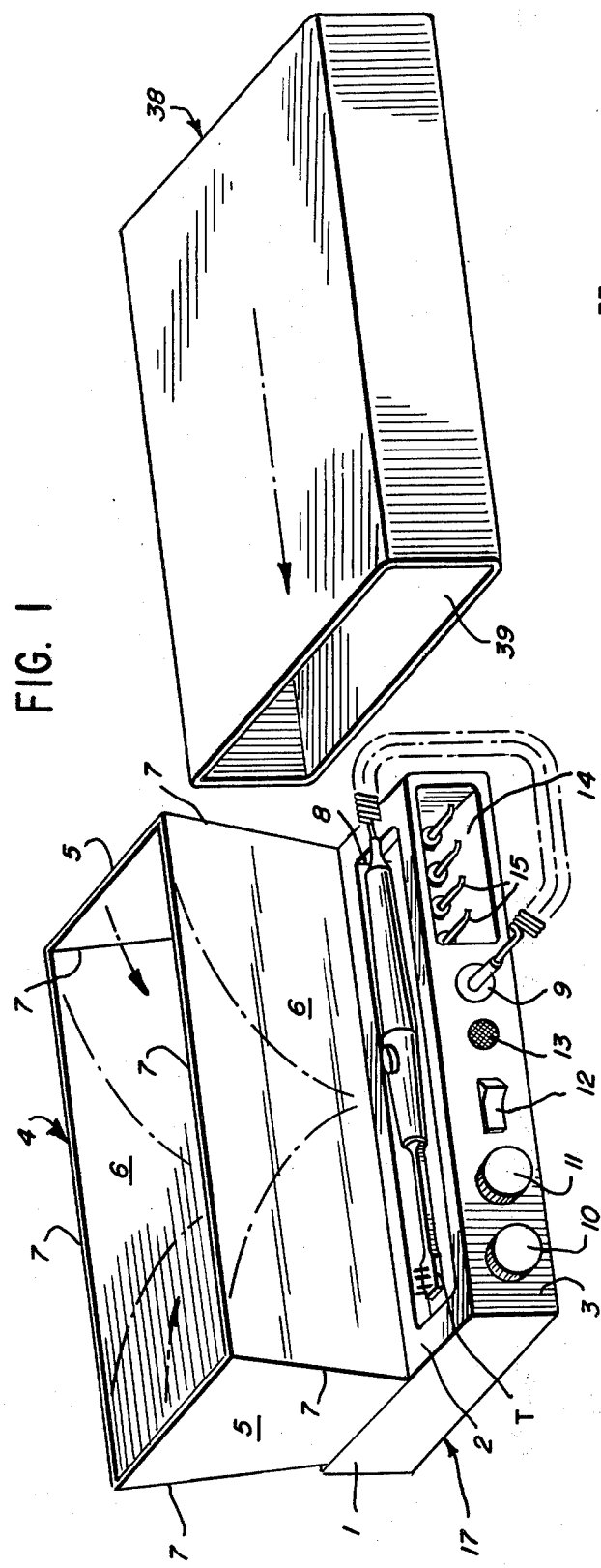
FIG. 1 is a perspective view of an appliance and carrying casing, or cassette, therefor, constructed in accordance with the invention, and showing the plastic container for liquid in its raised, or operative position on the appliance.

As shown in FIG. 1, the appliance has a box-type case 1, whose top 2 is constructed with inclined surfaces, slanting forwardly and downwardly towards the upright control face, or dashboard 3, so that the water in the liquid container 4 on a portion of said top surface 2 flows towards a discharge opening that communicates with an entry opening to the interior of said case 1.

The water container 4, permanent or removable, is mounted onto top 2. The opposed pairs of sides 5 and 6 of container 4 are formed mainly of flexible plastic sheets welded together at edges 7 to provide watertight seams. The container's edges 7 may be reinforced with resilient bows, or the pair of sides 6 may be reinforced with a non-flexible sheet of material. When the sides 6 are pressed down towards the top 2 of case 1, the flexible plastic sides 5 fold in the direction of the arrows (FIG. 1), so that sides 5 come to lie under the sides 6. The water container 4 is then in folded up condition. The sides 6 may be supplied with button-type snap fasteners, not shown but well known in the fastener art, so that the water container 4 will be maintained in place in folded condition.

On the inside, the sides 6 may be provided with an elastic spring bow that connects to the case 1 or to the bottom of the water container, so that the water container 4 will open automatically when the fastener is opened or when the enclosing cassette 38 is removed. Due to the action of the elastic spring bow, the sides 5 and 6 then move to their upright position seen in FIG. 1.

The case 1 has formed, in the lower, or forwardmost, part of the slanting top surface 2, a recess or cradle 8 which may be used to receive an electric toothbrush T (FIG. 1). A jack-type electric socket 9 for an electrical appliance, such as toothbrush T, is provided on the dashboard 3. When the electrical appliance T is connected, the engine part of the pump will be disconnected, as is known in the art of jack-type electrical connections.

On the dashboard 3, there are provided: a rotatable knob control regulator 10 for the dosing, or regulating the volume discharge, of the water; a rotatable knob control regulator 11 for controlling pulsation of the jet; a toggle-type on/off switch 12; and a lamp 13 which when illuminated indicates that the appliance is in operation.

Figure 3:
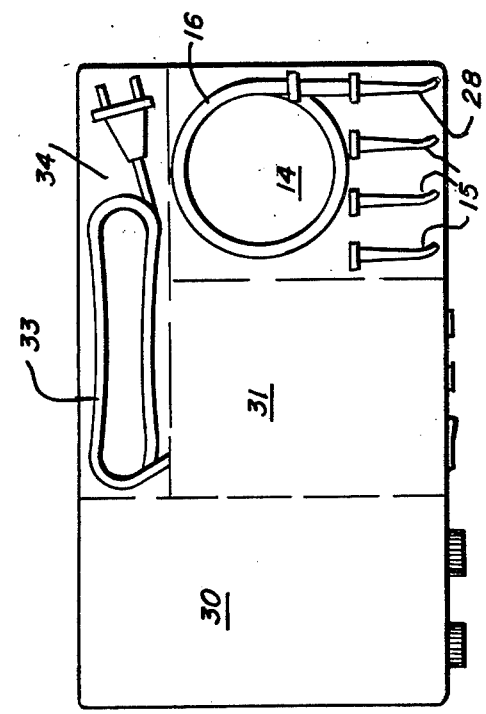
FIG. 3 is a schematic arrangement diagram of the appliance.

In the dashboard 3, there is an opening to a chamber 14, whose contents are illustrated in FIGS. 1 and 3 as including a plurality of spray nozzle attachments 15 and a coiled discharge hose 16. The nozzle attachments 15 are held in storage position for use by mounting clips. The supply end of hose 16 connects to a supply nipple within chamber 14.

A voltage selecting switch indicated generally by 17 in FIG. 1, as being on the underside of the case 1, is provided. Through this selecting switch 17, the appliance may be selectively conditioned to function at 100–120 V., or at 240 V., as is well known in the art.

Figure 2:
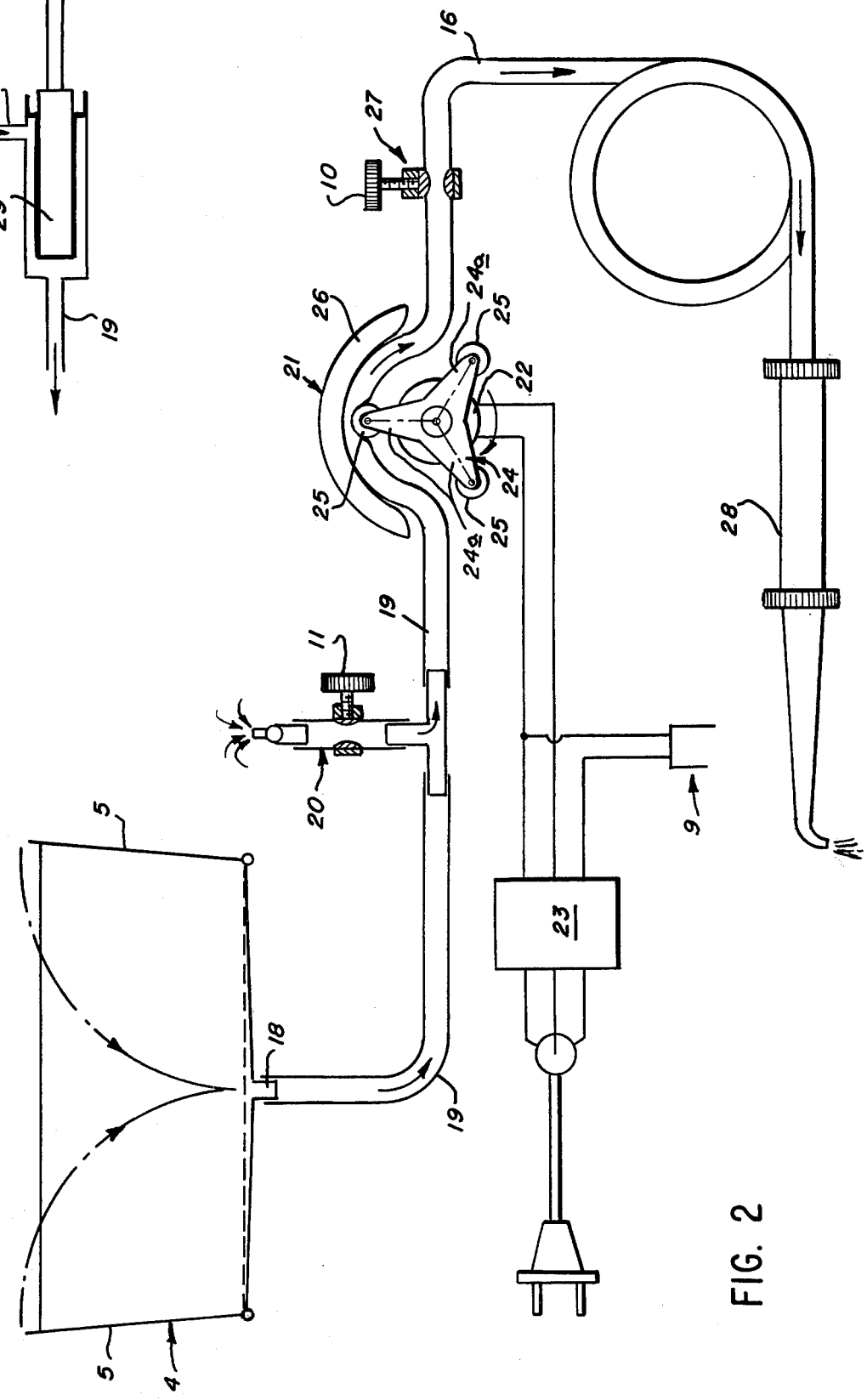
FIG. 2 is a schematic diagram of the appliance, illustrating mechanical folding of the liquid container, the hydraulic path of the liquid, and a typical electrical wiring for energizing portions of the appliance.

FIG. 2 shows a schematic operating diagram of the appliance. When the container 4 for liquids is filled with a supply of water, and the passageway between container 4 and case 1 is open, the water flows under gravity along the bottom slanting surfaces into the inlet nipple 18 and then through the hose 19 toward a pump. Between inlet nipple 18 and the pump, there is provided an air-inlet valve or aerator 20. Through valve 20, which is equipped with an automatic shut-off valve to prevent backflow of liquid, as is known in the art, air is drawn in as the water flows through hose 19, and the air-containing water then is conducted downstream toward the pump within the flow in the hose 19. In part as a result of the addition of air, the discharge of water from hose 16 will be interrupted or chopped providing a pulsating jet discharge from nozzle 28. The pulsating will be the stronger as the valve 20 is controlled to open wider to permit more aspiration of air into the column of water in hose 19. The opening of the valve 20 can be regulated by a screw control 11, so that a dosage of the pulsations is obtained in the easiest conceivable way with the adjustable screw control 11.

Instead of the heavy and expensive equipment used thus far in existing appliances, such as reciprocating piston pumps, rotary pumps or diaphragm pumps, a light hose pump 21 is used in this invention. A further advantage of the hose pump 21 is that the liquid being pumped cannot come in contact with the electrical parts. There is therefore no problem relative to waterproofing. The hose pump 21 is operated by a low-voltage, direct-current, motor 22, to which a transformer rectifier combination 23 is connected in series.

The size of the entire system is substantially reduced, in comparison with existing appliances for the same purpose, through the utilization of both a low-voltage small motor 22 and the specific type of hose pump 21; moreover, the operating parts are substantially lighter than it is the case with existing appliances which function with heavy motors and pumps.

In the light hose pump 21, the small low-voltage engine 22 rotates a propeller 24 that carries a plurality of spaced rotatable rollers or balls 25 at the ends of at least three equally angularly spaced propellers, wings, or arms 24a. The rollers 25 press against and into the wall of the flexible resilient hose 19 which is backed or supported by an arcuate abutment member 26 whose arcuate extent is greater than 120° arc relative to the axis of rotation of the propeller 24. The operation of each roller 25 in pinching, or compressing, hose 19 between the roller 25 and abutment 26, coupled with compressible aspirated air in the water column of the hose 19, and the arcuate length of abutment member 26 permitting two rollers 25 to simultaneously pinch hose 19 against abutment 26, operates to break the water column into slugs, or pulses, and to pressurize the air in the water slugs and to impel the slugs at the tangential velocity of the roller 25, so that downstream of the pump the water discharges at a high pressure in a pulsating jet.

A screw terminal 27 located downstream of pump 21 is used to dose or regulate the amount of water output which flows from pump 21 through the downstream discharge hose 16 before it reaches the spraying nozzle 28 that detachably connects to the discharge end of hose 16. The water output can be dosed simply by constricting hose 16 with a screw actuated terminal 27 under the control of knob 10.

Figure 4:
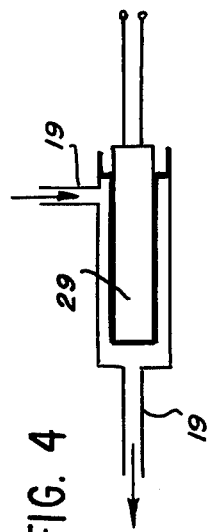
FIG. 4 illustrates schematically an alternative construction for a portion of the electrical circuit between the source of power and the pump's electric motor.

As an alternative to the transformer-rectifier combination 23, which supplies low-voltage current to the electric motor 22, it is possible to use a resistance heater 29 (FIG. 4) as a compensating resistance for the small low-voltage motor 22. The resistance heater 29 may be in the form of a cartridge that is arranged to be cooled by water bypassed from hose 19 which flows around heater cartridge 29. At the same time, the water from hose 19 will become lukewarm, which has for a result to cause the pulsating jet treatment of the teeth to be even more comfortable and more agreeable. The utilization of a heating resistor in lieu of the transformer also serves to reduce the weight of the appliance.

FIG. 3 illustrates a schematic construction diagram which shows, separated from each other within the case 1, a wet-cell 30, an electrical cell 31, and a storage chamber 14 for the hose 16, and the supply of interchangeable snap-on attachments 15. An electric supply cord 33 is stored in a laterally elongated recess 34 provided in the back edge of the appliance.

Figure 5:
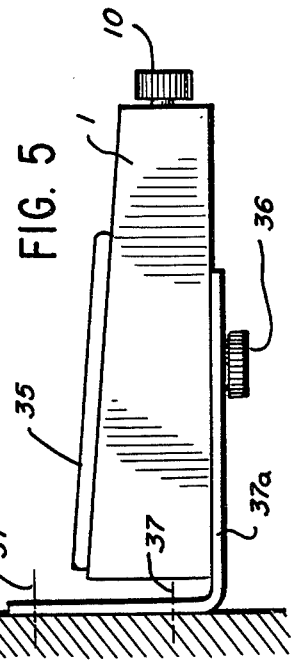
FIG. 5 illustrates in side elevational view the appliance with its liquid container folded, and the appliance supported from a wall mounted bracket.

FIG. 5 illustrates the appliance mounted on a wall and with the water container 4 folded up to the essentially flat packet condition shown at 35 lying on the casing's top side. The compactness, or relatively shallow height of the casing 1 is particularly impressive in the folded-up end view of FIG. 5. With a knurled-head retention screw 36, the appliance can be clamped onto a wall holder bracket 37a, which is wall mounted at 37 without any problem, which is a very practical construction.

FIG. 1 also shows a shell-like, rectangular, cassette 38 which is opened on one side 39. The cassette may be pushed or telescoped over the appliance when the water container 4 is folded up, so that the appliance is packaged in a handy and practical way, to provide a travel appliance that can be transported without any problem. The cassette 38 additionally may be used as a refill transport, to refill the container 4 with liquid.

From the foregoing description it will be understood that the appliance provides a pulsed jet of water which may be selectively directed by a spraying nozzle towards the teeth, or toward the intervals between the teeth, and/or toward the gums, which allows the teeth and the intervals between teeth to be cleaned at points, or localized regions, and the gums to be massaged at points too.

Figure 6:
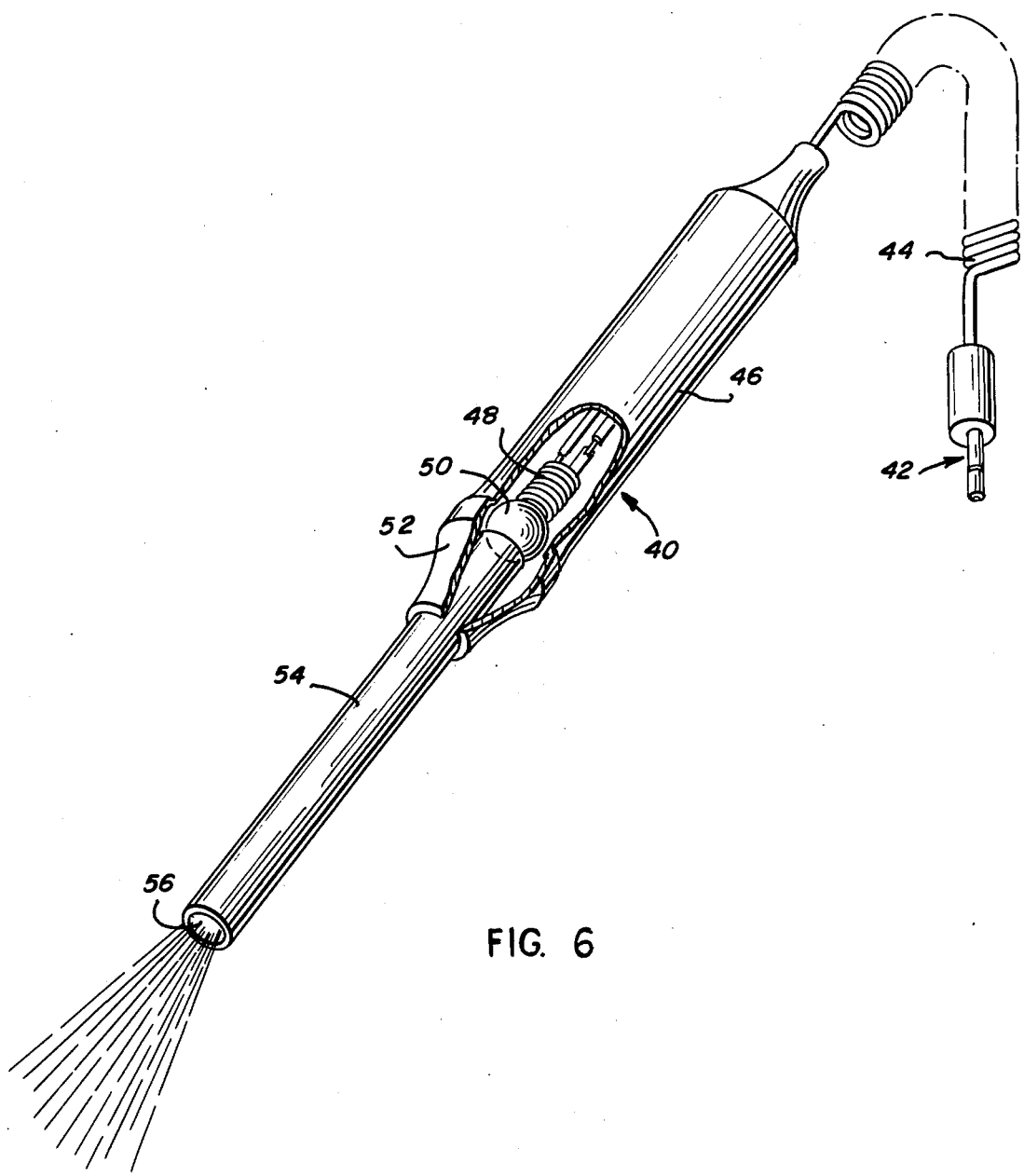
FIG. 6 is a perspective view, with portions broken away, of a light stick that can be used as an accessory for the appliance.

The improvement auxiliary feature of FIG. 6 may be used in an ancillary way to aid the principal purpose of the appliance and to increase the efficiency of the cleaning of the teeth and intervals between teeth at points, and in the massage of the gums, by providing a light source to throw light on the inside of the mouth, likewise at points, so that the spots to clean may be exactly recognized or checked after cleaning.

With the device of FIGS. 1-5 augmented by the improvement device of FIG. 6, the task of cleaning teeth and massaging gums is augmented with use of a lighting stick with its own light source, that connects by a permanent or removable connection to the appliance through an extensible electrical supply wire that is attached in such a way that the user can lead the lighting stick to his mouth or put it inside the mouth to obtain a locally-concentrated illumination at points of the individual parts of the mouth to be reflected in a mirror. The locally-concentrated illumination may be pointed correspondingly precisely as the pointing or directing of the jet of water from the mouth-shower appliance. The light source of the lighting stick, which is functionally designed as an incandescence lamp, can be energized through a feed wire which connects to the casing of the mouth shower, which is advantageous.

Thus, in FIG. 5, the light stick attachment, generally 40 includes at one end thereof a jack-type connector or plug 42 which is adapted to cooperate with an electric socket generally similar to socket 9 provided on casing 1, as shown in FIG. 1. Because the light stick attachment is to be functioning while the spray appliance is also functioning, the jack-type connector 42 and its socket have to be of a construction that does not interrupt operation of the pump means 21. The jack-type plug 42 is electrically connected through coiled extensible electric cord 44 to a cylindrical, hollow casing 46 that serves as a handle for the light stick 40.

Within handle-casing 46 there is a screw-type energizing socket 48, insulated from handle-casing 46, and adapted to receive a screw-in type lamp 50. An annular adapter 52 attached to the forward end of casing 46, secures therein the back end of a solid, cylindrical, conductor rod 54 made of plastic, preferably plexiglas. The character of the light conductor bar 54 is such that the light from lamp 50 passes principally longitudinally through the rod 54 with little, if any, light passing laterally through the bar 54, so that the light emitted from the front face 56 of bar 54 goes out as a focussed, or concentrated, illumination. Although the front face, or lighting terminus, 56 may be a flat surface, preferably, it will be slightly convexly rounded.

The lamp 50 for the lighting stick preferably will consist of a micro-high-tension lamp, which is a fluorescent lamp or a lumen. Although the lamp preferably is to be energized from the main electrical supply of the mouth-shower appliance, the lighting stick could be energized from another source. In any case, the principle purpose of the light stick is when coupled with a mouth-shower appliance.

Dentists are aware that it is more efficient during a dental treatment to illuminate the teeth and the mouth. Although the general concept of use of a light stick with cosmetic treatment is known in German reference D-OS No. 24 11 152, such a feature has thus far not been adopted in regard to teeth care at home.

In the care of teeth and gums, the use of a light stick permits a user of the mouth-shower appliance to direct the jet of water precisely onto the specific surface being illuminated, so that an exact cleansing is made possible, the surface which is illuminated being reflected, for instance, by the mirror of the bathroom.

The lighting stick 54 of FIG. 6 has such dimensions that it can easily be introduced in the mouth, and it creates an optimal focussed illumination, which is not possible with general light source.

The fact that the light stick is not itself permanently set into the case of the appliance, but that the stick itself is equipped with its own light source and an extensible energizing cable, gives the greatest possible freedom of movement. Also, the light stick makes precise examination after cleaning possible, to check if all food residues have been eliminated by the jet of water.

While one form of the invention has been described, it will be understood that the invention may be utilized in other forms and environments, so that the purpose of the appended claims is to cover all such forms of devices not disclosed but which embody the invention disclosed herein.

What I claim is:

1. In an appliance, for the cleaning and care of teeth and gums, that employs an electrically-driven pump means for discharging from the appliance a high pressure, pulsating, water jet, the improvement comprising, in combination:

a tube pump that includes an elongated flexible tube, along which a water column is to be moved, a backing member for a portion of the flexible tube, a rotor that includes arcuately spaced rollers for engaging, compressing and pinching portions of said flexible tube against said backing member to advance the water in the tube along the tube;

means for introducing air into the water in the tube upstream of the backing member of the tube pump;

the tube being resilient, whereby as the pump's rotor rotates, the water-air mixture is pressurized by a pair of spaced rollers that pinch the tube against the backing member, and the water-air mixture is then pressurized by compression of the compressible air therein, so that upon release of pressure of the leading roller against the resilient tube and backing member, the expanding compressed air in the water-air mixture expands to aid in providing a pulsating pressurized discharge of a water jet from the pump means.

2. An appliance as in claim 1 wherein the means for introducing air into the water column in said flexible tube is an aspirator which causes air to be drawn into the water as the water flows through the tube, and means including a control for manually selectively controlling the amount of air that is introduced into the water in said tube.

3. An appliance as in claim 1 including a means downstream of said tube pump for manually selectively controlling the amount of pressurized water discharged by the tube pump.

4. An appliance as in claim 1 wherein the rotor includes three equally spaced rollers for propelling water through said tube, and the backing member being arcuate with an arcuate length sufficient to permit only two rollers to simultaneously pinch the flexible tube against said backing member.

5. An appliance as in claim 1 wherein said electrically-driven pump means is driven by a low-voltage, system for the low-voltage motor being provided with a resistance heater serving as a compensating resistance for the low-voltage motor, and the water in the flexible tube being arranged to absorb heat from the resistance heater to provide heated water that is discharged from the flexible tube.

6. An appliance as in claim 1 wherein said electrically-driven pump means is driven by a low-voltage, direct current, electric motor; a lighting stick for providing selective, locally concentrated, illumination of portions of the teeth or gums that will be subjected to the high pressure water jet, said lighting stick including a low-voltage, micro-high-tension incandescent lamp whose illumination is conducted through an elongated rod of plastic to a lighting terminus; and transformer-rectifier means for supplying low-voltage direct current for energizing both said electric motor and said lighting stick.

7. In an appliance for treating teeth and gums with a pressurized, pulsating, water jet delivered from a refillable water container by tube means, pump means, and electric motor means, the improvement of a compact construction for such appliance, permitting same to be packaged and stored as a travel appliance, comprising in combination:
   a lower housing of substantially rectangular configuration with a substantially top planar surface, said lower housing being of a size adapted to house therein said tube means, pump means and electric motor means; and
   an upper, refillable, water-proof, foldable when inoperative, container having a bottom wall with a downwardly extending inlet nipple thereon, adapted for effecting flow communication from the interior of said container to the tube means in said lower housing, said container being substantially rectangular in cross-section and being provided with two pairs of opposed sides, a first pair of opposed sides being flexible to fold inwardly toward each other between the second pair of opposed sides, and the second pair of opposed sides being foldable toward each other to overlie the first pair of folded sides and to overlap to a flat folded condition toward and against said top surface of the lower housing.

8. An appliance as in claim 7 wherein edges of the sides of the foldable container are reinforced with resilient bows.

9. An appliance as in claim 7 wherein the container is of a size to be mounted on the top planar surface of the lower housing and wherein releasable means are provided on the second pair of sides of the foldable container for holding the water container in its inoperative folded condition.

* * * * *